United States Patent
Maiti et al.

(10) Patent No.: US 7,705,987 B2
(45) Date of Patent: Apr. 27, 2010

(54) FLUORESCENCE CORRELATION MICROSCOPY WITH REAL-TIME ALIGNMENT READOUT

(75) Inventors: Sudipta Maiti, Mumbai (IN); Sanjeev Kumar Kaushalya, Mumbai (IN); Kanchan Garai, Mumbai (IN); Jayaprakash Balaji, Mumbai (IN)

(73) Assignee: Tata Institute of Fundamental Research, Mumbai (IN)

( * ) Notice: Subject to any disclaimer, the term of this patent is extended or adjusted under 35 U.S.C. 154(b) by 0 days.

(21) Appl. No.: 11/816,387

(22) PCT Filed: Feb. 15, 2005

(86) PCT No.: PCT/IN2005/000015

§ 371 (c)(1),
(2), (4) Date: May 26, 2008

(87) PCT Pub. No.: WO2006/087727

PCT Pub. Date: Aug. 24, 2006

(65) Prior Publication Data

US 2009/0086204 A1    Apr. 2, 2009

(51) Int. Cl.
*G01N 21/25* (2006.01)
(52) U.S. Cl. .................................. 356/417
(58) Field of Classification Search ............... 356/317, 356/417; 359/380, 385
See application file for complete search history.

(56) References Cited

U.S. PATENT DOCUMENTS

| | | | |
|---|---|---|---|
| 5,815,262 A | 9/1998 | Schrof et al. | 356/318 |
| 6,582,907 B1 | 6/2003 | Epps et al. | 435/6 |
| 6,693,742 B1 | 2/2004 | Winterot et al. | 359/381 |
| 2002/0121610 A1 | 9/2002 | Tewes et al. | 250/458.1 |
| 2004/0151631 A1* | 8/2004 | Rigler | 422/82.08 |
| 2004/0257646 A1 | 12/2004 | Wachsmuth | 359/385 |
| 2005/0271549 A1 | 12/2005 | Janka et al. | 422/82.08 |
| 2006/0226374 A1* | 10/2006 | Rigler et al. | 250/458.1 |

FOREIGN PATENT DOCUMENTS

DE    10008594    8/2001

OTHER PUBLICATIONS

Foeldes-Papp et al., "Ultrasensitive detection and identification of fluorescent molecules by FCS: impact for immunobiology," *Proc. Natl. Acad. Sci. USA*, 98:11509-11514, 2001.
Maiti et al., "Fluorescence correlation spectroscopy: diagnostics for sparse molecules," *Proc. Natl. Acad. Sci. USA*, 94:11753-11757, 1997.

* cited by examiner

*Primary Examiner*—Tarifur Chowdhury
*Assistant Examiner*—Abdullahi Nur
(74) *Attorney, Agent, or Firm*—The Law Office of Michael E Kondoudis

(57) ABSTRACT

This invention relates to a confocal fluorescence correlation microscope with real-time alignment read out. With this instrument it is possible to do confocal imaging together with the particle size determination at a chosen location in the specimen. In particular, this invention relates to a detector module with a fixed aperture and detection electronics that can be conveniently connected to an existing confocal or multiphoton microscope, near the base of the objective lens of the microscope. This detector splits a part of the signal and uses it to generate a spot on the confocal image. This shows the spot where an FCS measurement can be carried out, and the same signal can then be used to perform a fluorescence correlation measurement after parking the excitation beam of the confocal to that spot. No alignment step is necessary for obtaining the measurement.

10 Claims, 6 Drawing Sheets

FLUORESCENCE CORRELATION MICROSCOPY WITH REAL-TIME ALIGNMENT READOUT

Figure 1:
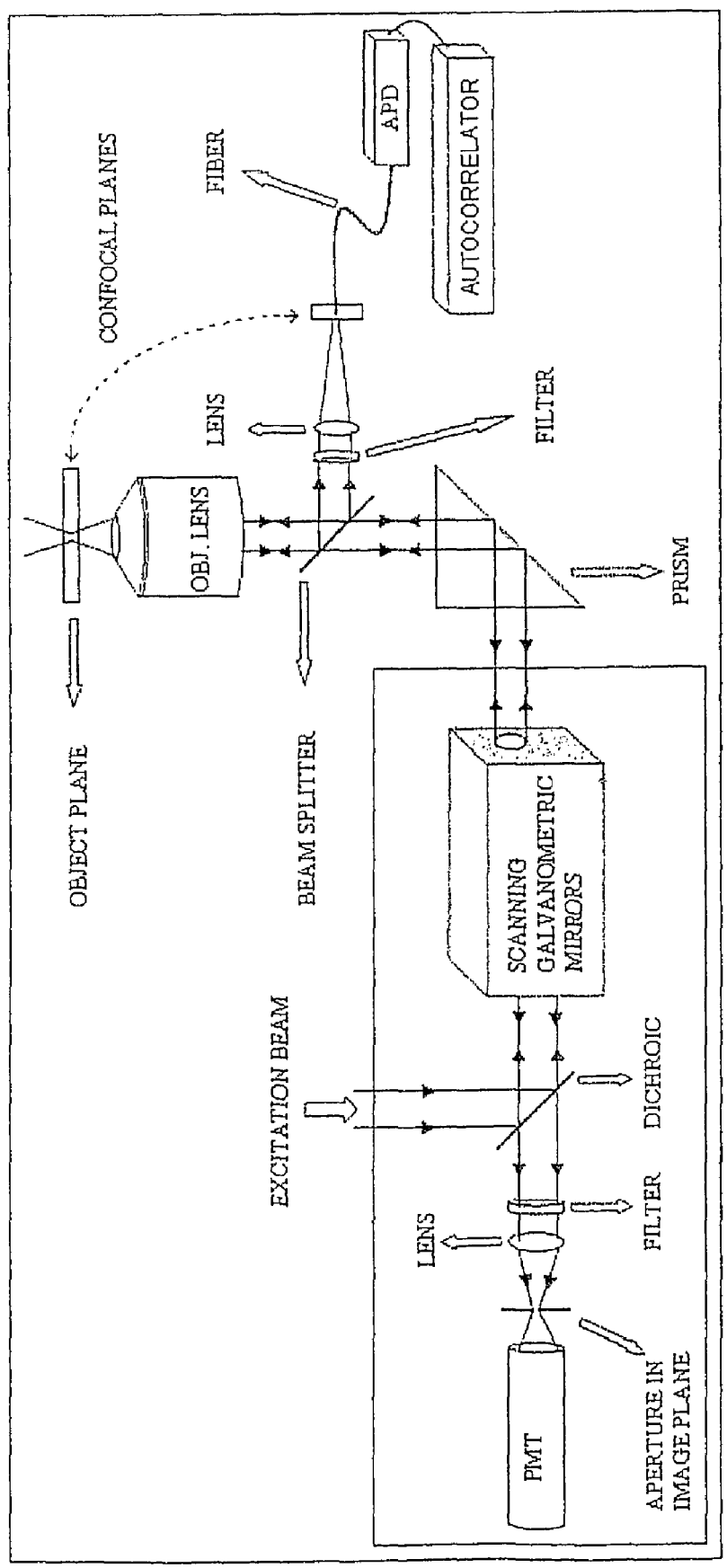

This application is a national phase application under 35 U.S.C. §371 of International Application No. PCT/IN2005/000015 filed 15 Feb. 2005, the entire text of which is specifically incorporated herein by reference without disclaimer.

FIELD OF INVENTION

This invention relates to a confocal fluorescence correlation microscope with real-time alignment read out, wherein the confocal microscope can be a typical confocal or multiphoton microscope. Fluorescence correlation spectroscopy is used to measure the size of the particles diffusing in the solution down to sub-nanometer resolution. Confocal fluorescence correlation microscope gives 3-D images of the specimen under test with the resolution of the wavelength of the laser light (usually hundreds of nanometers) used for imaging. Combination of these two devices makes an instrument with which it is possible to do confocal imaging together with the particle size determination at a chosen location in the specimen. It is popularly known as confocal fluorescence correlation microscopy.

PRIOR ART

Fluorescence correlation spectroscopy (FCS) was invented by Magde, Elson, and Webb in 1972. Marvin Minsky introduced the stage-scanning confocal microscope in 1957. Confocal laser-scanning microscope was developed by Aslund et al. Later, an augmentation of confocal microscope, the so called multiphoton microscope, was developed by Webb and coworkers. Gratton and coworkers performed FCS with two-photon excitation in 1995. Jovin and coworkers effectively combined a stage scanning microscope and a fluorescence correlation spectrometer in year 1998. Combination of confocal microscope and FCS is now available from multiple commercial vendors as described later in the text.

There are three main challenges in combining a confocal microscope with a fluorescence correlation spectrometer. First, the fluorescence detection in FCS needs to be highly sensitive; essentially, a single molecule detection sensitivity is desired.

This is typically not possible in a confocal microscope. Secondly, when a location is chosen from the confocal image for FCS study, it needs to be ensured that the FCS measurement is actually performed at that chosen location. Finally, the optical design needs to be versatile enough so that it is applicable for both confocal and multiphoton excitation.

There are three demonstrated ways of combining confocal microscopy with fluorescence correlation spectroscopy.
(1) Using the same fluorescence pathway as the confocal microscopy. Only the confocal microscope detector is typically replaced with a higher sensitivity detector. In this scheme the fluorescence passes through the scanning optics of the confocal microscope unit. In one implementation, a sliding mirror switches the fluorescence between the confocal imaging detector and the FCS detector, according to what is needed.
(2) Using a separate FCS unit. Here the emitted fluorescence enters directly to a separate FCS unit without passing through the scanning optics. The image seen by the confocal detector and the FCS detector needs to be prealigned and this alignment needs to be maintained.
(3) Using a stage scanning confocal microscope unit. No laser beam scanning is employed in this scheme.

There are at least three commercially available systems:
In the first instrument viz
Zeiss ConfoCor 2/LSM 510 combi, from Carl Zeiss, Germany the second method is used. The FCS unit is pre-aligned to a fixed spot in the object space whose coordinates are stored in the computer. When the user chooses a location in the confocal image for FCS measurements, a high resolution motorized specimen stage moves that location of the specimen to this pre-aligned fixed location. Collection efficiency of FCS unit is good as the path length of the fluorescence from the specimen to the detector is small. Also light does not pass through too many optical elements, so reflection losses are kept to a minimum, improving the collection efficiency.

However, this system suffers from the following disadvantages:
(i) In this scheme one has to rely on the stability of the fixed alignment between the confocal and the FCS units, as there is no real verification of where exactly the measurement would be carried out. This "fixed" alignment needs periodic calibration.
(ii) It needs to use a high resolution automated stage which increases the cost and complexity of the instrument.
(iii) It cannot combine confocal and "non-descanned" (i.e. higher sensitivity) multiphoton detection.

The second commercially available instrument viz Leica TCS SP scanhead with FCS extension uses the first method. The fluorescence for FCS is collected after it traverses through the confocal aperture in the scanning unit. Since the fluorescence reaches both the confocal imaging detector and the FCS detector after it has passed through the same aperture, it is likely that the alignment between these two detectors are reliably maintained. So directly the excitation beam can be parked at any location of the specimen and an FCS measurement can be obtained from there. It doesn't need any high resolution automated stage.

However, this instrument also suffers from the following drawback.

Fluorescence passes through the scanning optics, and many other optics in the confocal scanning unit, which lowers the sensitivity of FCS. The path length to the detector is long, which further lowers sensitivity for scattering specimens. Also, non-descanned multiphoton measurement cannot be performed.

The third commercially available instrument is ALBA FCS from ISS. This employs scheme number 3. The positioning of the detectors can be accurate and the beam need not pass through scanning optics, as there are no scanning optics in the instrument.

A major drawback of this scheme is the slow rate at which the images are acquired. A heavy microscope stage moves at a much slower rate than a scanning mirror. This is precisely the problem that was solved by the invention of laser scanning by Aslund.

US patent application 20020121610 describes a fluorescence correlation spectroscopy module for a microscope which has a separate FCS detection unit where a pinhole array is stably pre-aligned with, and can be connected with a typical fluorescence microscope.

U.S. Pat. No. 5,815,262 teaches an apparatus for carrying out laser-induced two-photon fluorescence correlation spectroscopy (TPA-FCS), in which a plurality of volumes (6) are delimited or defined in the apparatus in such a way that samples (3) introduced into these volumes can be excited and observed in parallel by means of a single laser (1). Such an apparatus can be used to screen active compounds.

OBJECTIVES OF THE INVENTION

The main objective of the present invention is to propose a high sensitivity confocal florescence correlation microscope instrument which provides an automatic real time read out of the location where FCS measurement would be performed.

Yet another object of the present invention is to propose an instrument which does not rely for its sensitivity on the accuracy and stability of a prior alignment.

Still another object of the present invention is to propose an instrument whose optical path length is small.

Further object of the present invention is to propose an instrument wherein fluorescence goes directly to a separate FCS unit without much reflection losses thus ensuring high sensitivity of the system.

Yet further object of the present invention is to propose an instrument which does not require the automated high accuracy translation stage thereby to reduce the cost and complexity of the instrument.

Still further object of the present invention is to propose an instrument by which high sensitivity confocal detection can be performed without change in the alignment of the detection path.

Another object of the present invention is to propose an instrument which can be used to determine the point spread function of confocal microscope inside the actual specimen.

Yet another object of the present invention is to propose an instrument which is comparatively smaller in size.

Still another object of the present invention is to propose an instrument in which there is minimal loss of fluorescence signal due to scattering and reflection in scanning optics.

Still another object of the present invention is to have a continuous visual display of the location in a confocal image where the FCS measurement can be performed.

Further objects and advantages of the present invention will be apparent from the following detailed description.

SUMMARY OF THE INVENTION

According to the present invention there is provided a confocal fluorescence correlation microscope comprising a combination of fluorescence confocal microscope providing 3-D fluorescence images of the sample with the resolution of the wavelength of the laser light and a fluorescence correlation spectroscope for FCS measurement of the size of fluorescent particles present within the imaged area of the specimen.

One aspect of the present invention relates to a confocal fluorescence correlation microscope for real time alignment read out of the confocal image for performing FCS measurement of a specimen. This comprises of a fluorescence confocal microscope, a fluorescence correlation spectroscope, a beam splitter placed in the microscope slider assembly at the base of the objective lens to receive the fluorescence emitted by the specimen and split it into two parts, at least one optical filter placed close to the beam splitter, preferably within 0.5 m of the beam splitter, an optical lens placed adjacent to the filter along the focus plane of the lens for focusing the beam, at least an optical fiber coupled to a detector held in pace by an appropriate holder in the focal plane of the image, at least one fluorescence detector preferably APD detector for producing an electric pulse for each photon detected from the collected fluorescence carried through an optical fiber, preferably an electronic buffer circuitry to protect the detector, and a signal processor (preferably a digital correlator) which accepts the output of the detector for performing FCS measurements.

Another aspect of the present invention relates to a process for FCS measurements with the confocal fluorescence correlation microscope comprising of the following steps:

a) exciting the specimen with a laser beam for emission of fluorescence
b) Collecting the fluorescence from the specimen by the objective lens;
c) Splitting the fluorescence with the beam splitter into two parts: transmitted fraction and reflected fraction;
or, as an alternative to step c), where the fluorescence is split sequentially and not simultaneously. This alternative is less preferred for a typical confocal microscope but more preferred for a multiphoton microscope.
d) Passing the transmitted fraction through the optics of the confocal microscope, scanning the transmitted fraction through galvanometric mirrors, filtering the fraction through a filter; passing the filtered fraction through a lens to a PMT detector for generating the confocal image;
e) Passing the reflected fraction through the filter, lens, to the optical fiber present along the plane of focus, coupled with a high sensitive Avalanche photodiode (APD) detector, splitting the electrical output of the APD detector into two parts preferably through an electronic buffer, and feeding one of the output to one of the input channels of the confocal microscope and also in parallel to an autocorrelator; The reflected fraction can also be split into more than one part for multicolor detection, with each part following essentially the design outlined above.
f) Scanning the object plane by the confocal excitation beam and scanning the transverse image plane containing the fiber by the focused fluorescence
g) Generating a spot image from the fiber input channel to the confocal microscope and full image of the object by the transmitted part going to another channel of the confocal microscpe.
h) Merging the images from both these channels showing an image with a spot.
i) Moving the specimen in real time, so that this spot is moved to the desired position where FCS measurement is required
j) Parking the scanning beam at the desired spot in the specimen.
k) Making the FCS measurement at the desired location in the image by activating the correlator and feeding the output of the correlator to the signal processor.

In another embodiment of the present invention, the reflected fraction is split into more than one part for multicolor detection with each part following the design outlined above.

In yet another embodiment of the invention, the reflected fraction is sent to the confocal detector, while the transmitted fraction is sent to the fiber input to the APD, with each part following essentially the design outlined above.

At the outset of the description, which follows it is to be understood that the ensuing description only illustrates a particular form of this invention. However, such a particular form is only an exemplary embodiment and without intending to be understood as exemplary teaching of invention and not intended to be taken restrictively.

DESCRIPTION OF THE ACCOMPANYING DRAWINGS

According to the preferred embodiment, the present invention is illustrated through the following drawings:

FIG. 1 gives the schematic diagram of the confocal correlation microscope.

Figure 2:
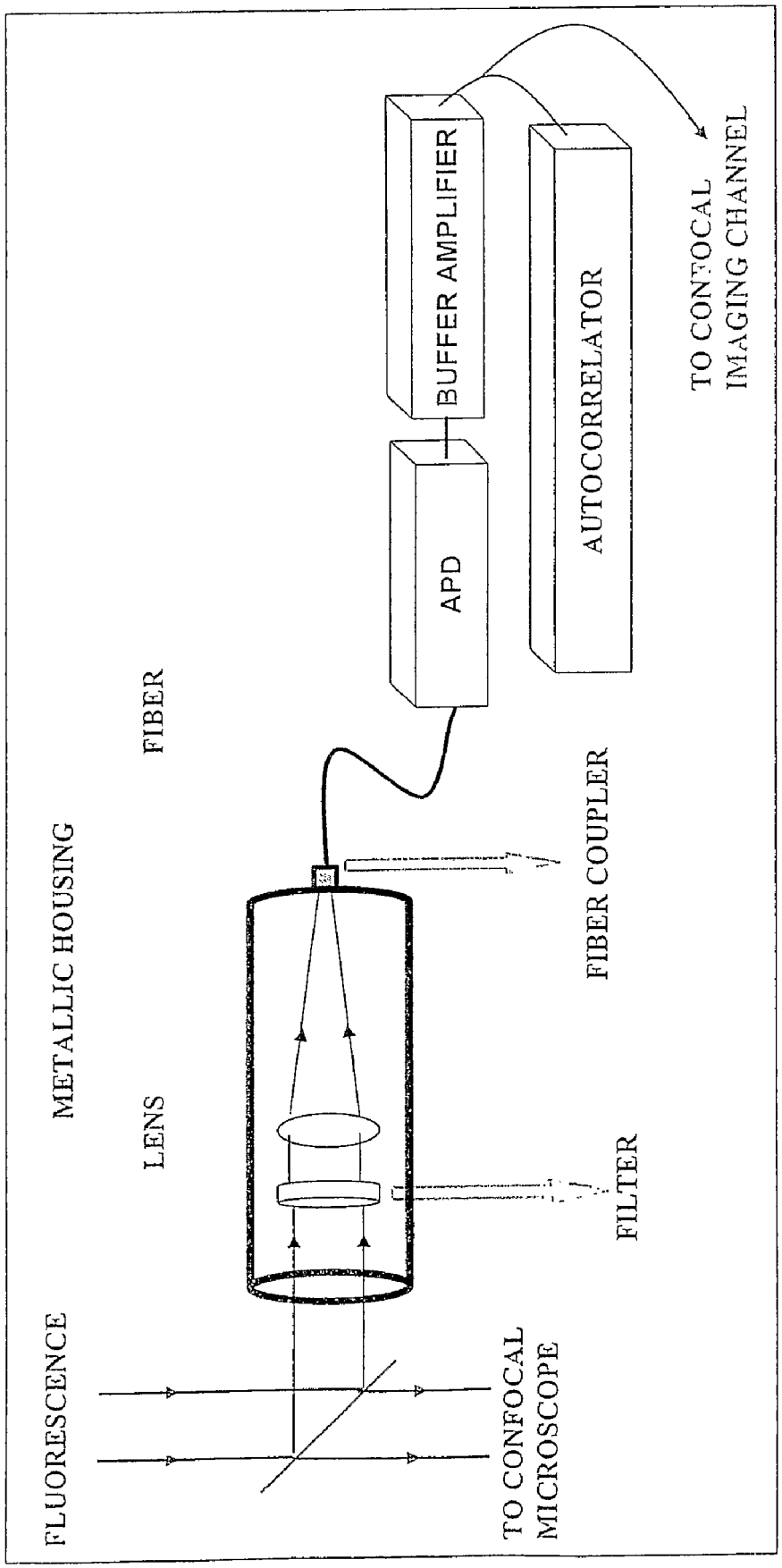

FIG. 2 gives the schematic diagram of the novel features of the invention.

Figure 3:
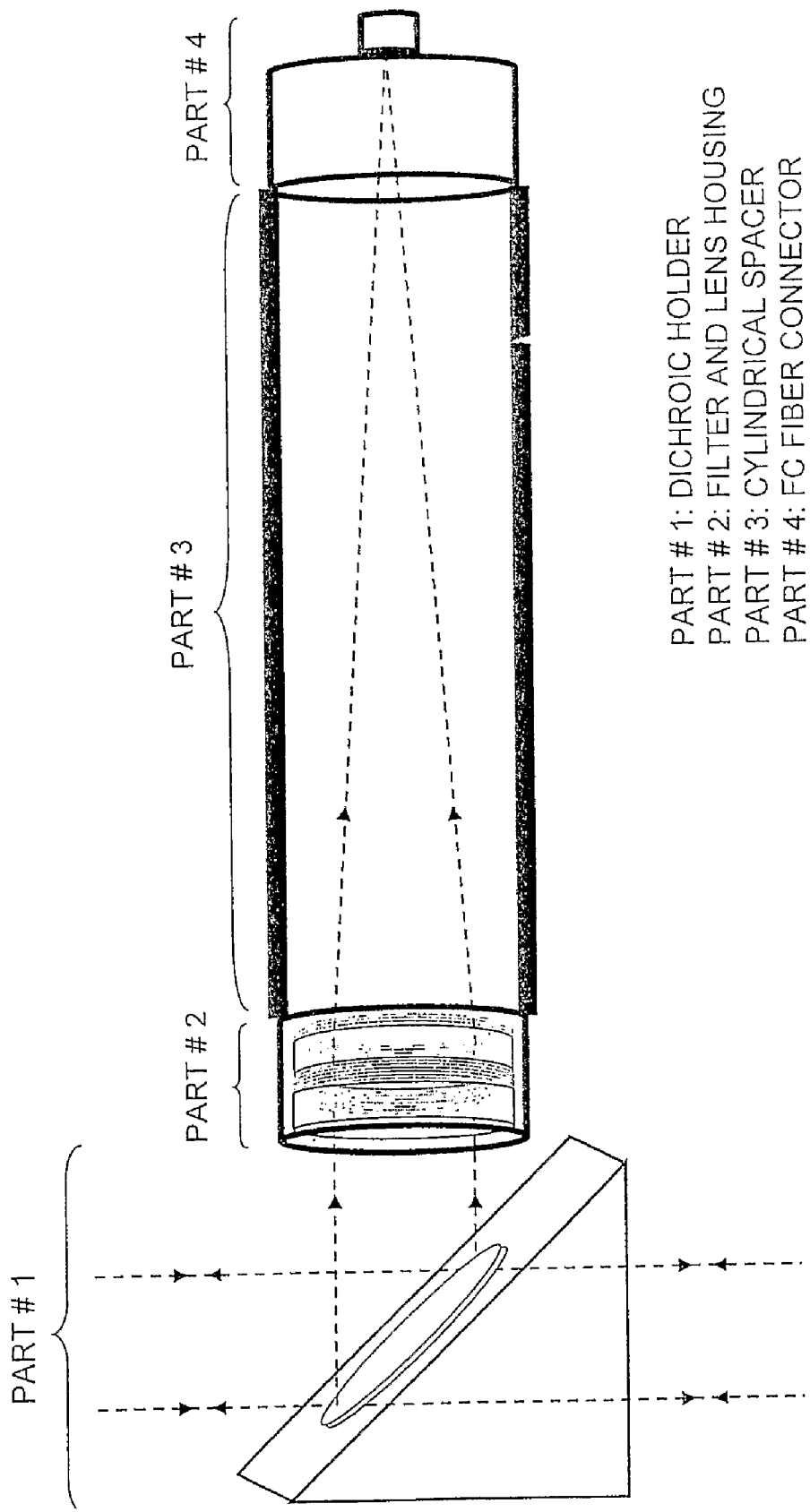

FIG. 3 gives the details of metallic housing containing dichroic, filter, lens and the fiber.

Figure 4:
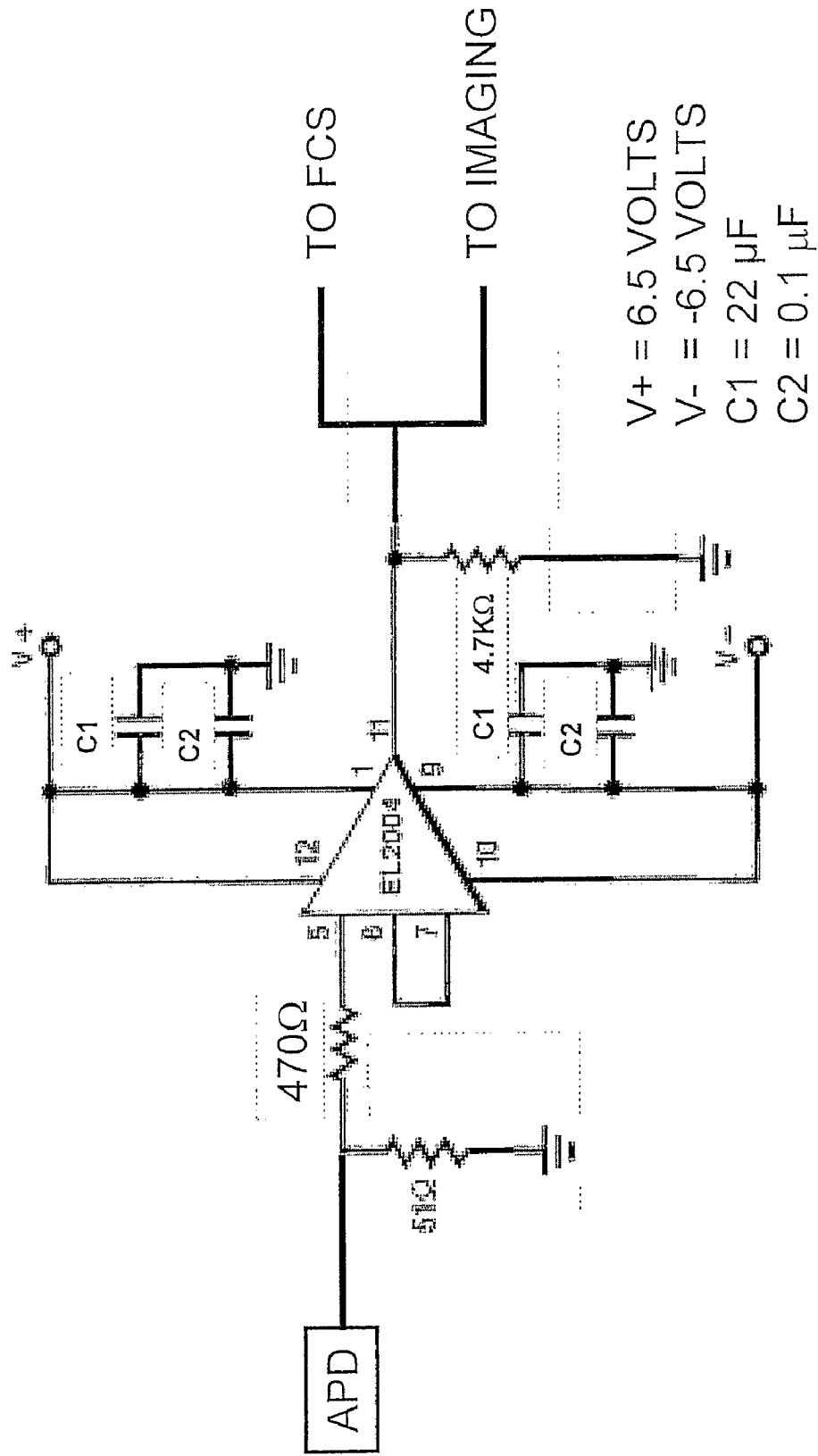

FIG. 4 gives the details of the electronic buffer circuit which is preferably used for protecting the detector.

Figure 5:
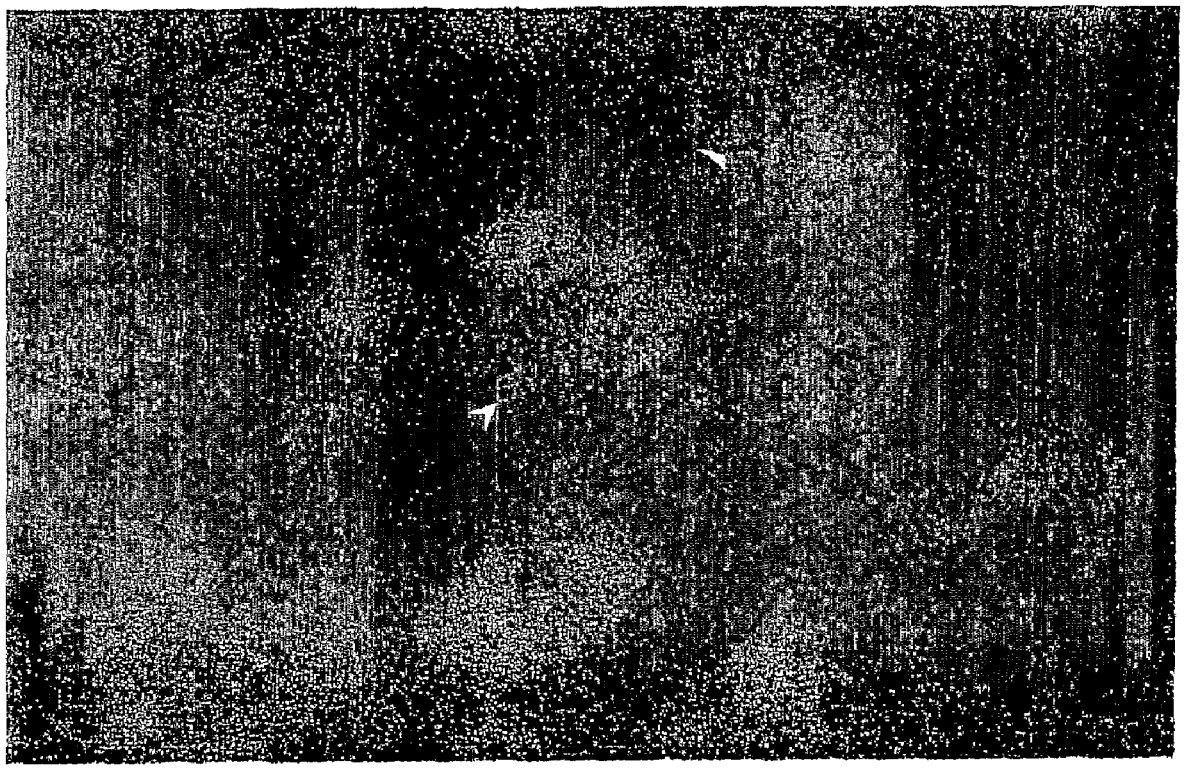

FIG. 5 shows an example of the merged image from FCS and imaging detectors.

Figure 6:
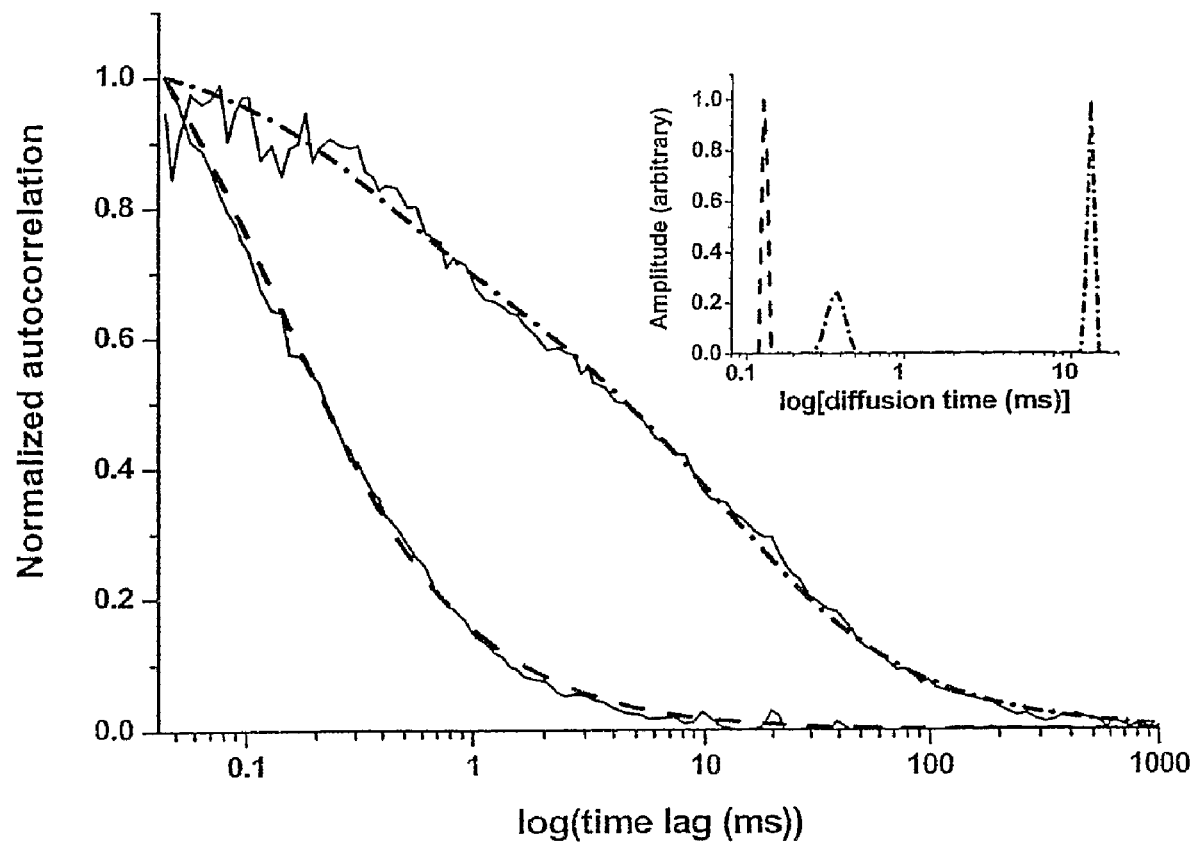

FIG. 6 gives an example of the graphical representation of correlation data and fits obtained from the specimen.

The beam splitter as shown in FIG. 1 splits the signal fluorescence light into two parts. One part travels to the apertured detector for FCS, the other to the imaging detectors of the confocal microscope. The splitting ratio of the splitter (for fluorescence light) can vary such that between 10% to 70% of the light goes to the imaging detector. A smaller ratio (towards 10%) makes the image quality poorer and the FCS data quality better, and vice versa. The splitting mirror may be colour dependent. For the excitation light, the splitter should pass more than 25% of the light, and ideally should pass as close to 100% of the light as practicable. The angle that the beam splitter makes with the fluorescence beam coming from the objective lens should be around 45 degree for best results, but angles between 30 to 60 degrees would work.

The FIG. 2 shows the detector which should preferably be of the single photon counting type. It should be able to produce an electrical (either voltage or current) for each photon detected. Better detection efficiency (usually termed the quantum efficiency of the detector) would yield better results, but a detection efficiency of at least 10% is required for satisfactory operation. The detector should be fast, that is, a photon arriving after a microsecond (or later) after the previous photon should be detectable as a separate photon by the detector. Amongst the currently available technologies, a single photon counting avalanche photodiode with up to 70% detection efficiency best suits the requirements of the apparatus. The detector should have low inherent noise, and it should not count more than 1000 photons per second in absence of a real signal.

The Autocorrelator or the signal processing unit as shown in FIG. 2 should be able to record the signal from the detector and communicate these results to a personal computer. The computer should be able to accept data at a high rate, at least a 100,000 inputs per second, from the detector. The computer itself, or digital signal processing board, performs an autocorrelation of the detected temporal pattern of the photons (as defined in Maiti et al., Proc. Natl. Acad. Sci. USA, 1997). Currently, a digital signal processing board able to perform a fast autocorrelation is the best option.

The detector signal output is fed in parallel to the signal processing unit for performing the autocorrelation, and to an input channel of the confocal imaging microscope. A typical confocal microscope has multiple detection channels, which can receive signals from its own "internal" photodetectors, or optionally, also from external photodetectors. The confocal microscope used in conjunction with this apparatus has (at least) one of its channels connected to the "internal" detector that receives one part of the signal that is split by the splitter. Another channel receives signal from the apertured FCS detector that is a part of this apparatus and which receives the other part of the split signal. The data processing machinery of the confocal detector displays the signal received from both of these channels as separate images. The image from the internal detector is similar (albeit less bright due to splitting) to the image that would normally (that is without our apparatus attached to the confocal microscope) be obtained from the same specimen. The image from the other detector consists of a spot, due to the fact that the signal beam is scanning the aperture in front of the external detector. The image processing abilities of the confocal microscope is utilized to merge these two images together, which reports the location of the aperture with respect to the specimen.

DETAILED DESCRIPTION WITH REFERENCE TO THE ACCOMPANYING DRAWINGS

In accordance with the present invention, one of the embodiment of the present invention consists of a confocal scanner (MRC 600, Bio-Rad) coupled with an inverted microscope (eclipse TE300, Nikon, Japan) and a He:Ne laser (1.2 mW at 543.5 nm, Jain Laser Technology, India) for excitation. In the confocal scanner a dichroic (560DCLP, Chroma Inc.) is used to separate the excitation and the emission beams. The fluorescence is split for FCS just before the objective lens (60×, 1.2 NA, water immersion, Plan-Apo, Nikon, Japan) with a 70/30 beam splitter (Chroma Inc.) placed in the dichroic "slider" box of the microscope. 30% of the fluorescence is focused with an achromat lens (F=250 mm, Newport, USA) onto a plane containing a 60 um core diameter multimode optical fiber (Newport, USA). The FCS detection housing has an aluminium plate containing the fiber which is kept within approximately 0.5 mm of the focus plane. The FCS housing is an aluminium cylinder that holds the achromat lens and a filter (HQ645/110, Chroma Inc.). The fiber is coupled to a single photon counting avalanche photodiode (APD) detector (SPCM-AQR-150, Perkin-Elmer). The rest 70% of the fluorescence reaches the normal detector of the confocal microscope after traveling back through the galvanometric scanning mirrors and an emission filter (D625/30, Chroma Inc.) (FIG. 1) Images are taken from both the channels (the APD and the internal confocal PMT detector) simultaneously and merged (FIG. 5). The sample is positioned so that the APD spot falls on a part of the membrane that is not very bright, in order to have a low number of fluorophores in the probe volume. Location of the spot is read by the software and the beam is parked to the same point in the sample. The output of the APD is fed to the digital autocorrelator (ALV-5000, ALV-Laser V.m-b.H, Germany) and an FCS measurement is performed.

The principle behind the FCS measurement is as follows. The fluorescence collected from the specimen by the objective lens is split with a beam splitter, placed in the microscope 'slider' assembly at the base of the objective (FIG. 1). The transmitted fraction travels back to the normal confocal detector through the scanning mirrors and the pinhole. This is used for generating the confocal image in one of the imaging channels. The reflected fraction of the fluorescence is focused with a lens. The plane of focus contains an optical fiber (with a diameter approximately equal to the Airy disc of the focused spot) at an arbitrary location. The light from the fiber is coupled into a high sensitivity detector whose output is fed separately to one of the input channels of the confocal microscope, and in parallel to a hardware signal correlator. While the confocal excitation beam scans the object plane, the focused fluorescence spot also scans the transverse image plane containing the fiber face. During each X-Y scan, the focus moves through the fixed fiber face, generating a momentary signal. Therefore the image from the fiber channel consists only of a small spot, while the fraction which goes to the confocal system generates the full image of the object. When the images from the two channels are merged, it shows a normal confocal image with a spot on it. While the imaging is going on, this spot can be moved in real time to any desired location of the image by manually moving the sample stage. For performing the FCS measurement, the location of the spot is read from the image and the scanning beam is parked at this location. Since the spot automatically marks the location that the collecting fiber is confocally aligned to, the output of the hardware correlator now provides the FCS measurement at this location. This scheme thus achieves automatic FCS alignment by exploiting the capability of parking individual scanning mirrors of the confocal microscope to any desired position, obviating the need for a separate mechanized stage. But most importantly, it provides a real time feedback for the location of the sample where the FCS measurement would be done. This principle is also applicable for a multiphoton microscope.

It will be apparent to those skilled in the art that various modifications and variations can be made to the process and the apparatus of the present invention without departing from the spirit or scope of the invention. Thus, it is intended that the present invention covers the modifications and variations which may be obvious to the people skilled in this field. Some of these can be modifications made in following parts.
i) Filters: Multiple filters can be used instead of a single one. This may be necessary to make the rejection of background light stronger in some cases. Also the filter may be placed after the lens, anywhere between the lens and the aperture (fiber).
ii) aperture: a convenient arrangement is to use an optical fiber as the aperture. However, a physical aperture (e.g. a hole in a plate) can also be used instead of a fiber.
iii) Instead of connecting the detector output in parallel to the confocal and the autocorrelator (signal processing unit), the signal can be first connected to the imager, an image generated, and then the connection can be removed from there and put into the signal processor.
iv) The confocal microscope can be a "typical confocal", or a "multiphoton microscope".
v) There can be multiple detectors detecting different emission colours separately. This can be achieved by adding a second splitter in our apparatus which can separate two different colours emanating from the specimen. Then an autocorrelation can be performed on each individual channels, and/or a cross-correlation can be performed on the two signals obtained from the two detectors.

EXAMPLE

RN46A Cells were incubated in 10 nM Nile red contained in Thomson's buffer (composition in mM:HEPES 20, $Na_2HPO_4.2H_2O$ 0.3, $KH_2PO_4$ 0.4, NaCl 146.1, KCl 5.4, $CaCl_2.2H_2O$ 1.8 $MgSO_4.7H_2O$ 0.8, glucose 5.0) for three minutes, and then washed thrice with clear buffer.

FIG. 5 shows the image of the cells (green) together with the spot (red) formed by the pinholed external APD detector. The beam is then parked at this location. A 60 second (three runs) accumulation of the data yields the autocorrelation curves as shown in FIG. 6. The figure shows two curves: one (dash) for 5 nM Nile red solution in the buffer (above the cells) and another (dash dot) is for a location on the cell membrane. The curve is fitted by the MEMFCS analysis routine (FIG. 6 inset). This routine fits the data to the widest possible distribution of diffusion times that is consistent with the errors in the data, eliminating bias in the fitting routine. In the solution (dashed curve) we obtain a narrow distribution (indicating a single diffusing species) centered at 0.126 ms. In the membrane (dash and dot curve) we get two components, one at 0.360 ms and another with higher amplitude at 13.0 ms. The smaller amplitude may be due to the diffusion of free Nile Red dye inside the cytoplasm. Because excitation volume is much bigger than the membrane thickness some part of the signal unavoidably arises outside the membrane also. The longer component (13.0 ms) is ascribed to the Nile Red in membrane. It is found that the diffusion constant in the membrane is nearly—100 times larger than that of the buffer, yielding a relative viscosity of the membrane of the order of 100, which is reasonable.

Present method is different from scanning correlation spectroscopy, which also is performed on a confocal microscope. Scanning FCS either does not measure diffusion or at best does it with nearly—ms time resolution. This makes these techniques inappropriate for measuring diffusion of small fluorophores, such as GFP, inside the cytoplasm (typical diffusion times of nearly—100 μs through the probe volume). The method presented here is equivalent in time resolution and optical sensitivity to the best available stand-alone FCS instruments, which are fixed excitation point APD coupled devices.

The invention claimed is:
1. A high sensitivity confocal fluorescence correlation microscope for real time alignment read out of a confocal image for performing FCS measurement of a specimen, comprising:
 a fluorescence confocal microscope;
 a fluorescence correlation spectroscope; and
 a beam splitter selectively placed in the microscope slider assembly at the base of the objective lens and ahead of the scanning optics of said microscope to receive the fluorescence emitted by the specimen placed on a movable sample stage and split it into transmitted part and reflected part, wherein the transmitted part travels to imaging detectors of the confocal microscope for image generation via said scanning optics and the reflected part, which is non descanned and thus a high sensitivity signal, travels separately to an apertured detector for the FCS measurements,
 wherein said apertured detector for FCS measurement comprises means for generating an image of a focused spot and for performing the FCS measurement and comprises:
 at least one optical filter placed within operable proximity of the beam splitter;
 an optical lens placed adjacent to the filter along the direction of the reflected fluorescence beam for focusing the beam;
 an optical fiber coupled to at least one fluorescence detector for producing an electric pulse for each photon collected through the optical fiber and also generate said spot image,
 wherein said fluorescence detector output includes said spot image and is fed separately to one of the input channels of the confocal microscope and also in parallel to a correlator,
 wherein the said confocal microscope is adapted to merge its images with said spot image to produce an image with a spot and having the means for moving the specimen in real time and parking the scanning beam at a desired spot in the specimen, and
 wherein said correlarator is adapted to carry out the FCS measurement at the desired location in the image and feeding the output of said correlator to a signal processor for performing said FCS measurement.
2. The confocal fluorescence correlation microscope of claim 1, wherein the at least one fluorescence detector is further defined as an APD detector.

3. The confocal fluorescence correlation microscope of claim 1, wherein the signal processor is fed by the output of the detector through an electronic buffer amplifier.

4. The confocal fluorescence correlation microscope of claim 1, wherein the beam splitter is a dichroic or a partially reflective mirror.

5. The confocal fluorescence correlation microscope of claim 1, wherein the fluorescence correlation spectroscope comprises a cylindrical metallic housing having an achromatic lens and a filter.

6. The confocal fluorescence correlation microscope of claim 1, wherein the optical fiber is held in place by a metallic plate provided in a metallic housing, where the metallic plate containing a multimode fiber is held near the focal plane of the achromatic lens placed in the path between the beam splitter and the fiber.

7. The confocal fluorescence correlation microscope of claim 1, wherein the fluorescence detector comprises a single photon counting avalanche photodiode.

8. The confocal fluorescence correlation microscope of claim 1, wherein the reflected fraction of the splitted beam is further splitted into more than one part for multicolour detection with each part following essentially the same design.

9. The confocal fluorescence correlation microscope of claim 1, further defined as adapted to detect different emission fluorescence colors separately for multiple detection via a plurality of splitters and autocorrelation performed on each individual channel and/or cross-correlation performed on signals obtained from two detectors.

10. A process for FCS measurement with a confocal fluorescence correlation microscope of claim 1 comprising:
   a) exciting a specimen with a laser scanning beam for emission of fluorescence;
   b) collecting the fluorescence from the specimen by the objective lens;
   c) splitting the fluorescence simultaneously or sequentially with the beam splitter into two parts, transmitted fraction and reflected fraction;
   d) passing the transmitted fraction through prism, scanning the transmitted fraction through galvanometric mirrors, filtering the fraction through a filter, passing the filtered fraction through a lens to a PMT detector for generating the confocal image;
   e) passing the reflected fraction through the filter, lens, to the optical fiber present along the plane of focus, coupled with a high sensitive APD detector and feeding the output to one of the input channels of the confocal microscope and also in parallel to a autocorrelator;
   f) scanning the object plane by the confocal excitation beam and scanning the transverse image plane containing the fiber by the focused fluorescence;
   g) generating a spot image from the fiber channel to the confocal microscope and full image of the object by the confocal microscope;
   h) merging the images from both the channels to produce an image with a spot;
   i) moving the specimen in real time to any desired position where FCS measurement is required;
   j) parking the scanning beam at the desired spot in the specimen; and
   k) making the FCS measurement at the desired location in theimage by activating the correlator and feeding the output of the correlator to the signal processor.

\* \* \* \* \*